United States Patent
Graves et al.

[11] Patent Number: 6,096,024
[45] Date of Patent: *Aug. 1, 2000

[54] BLUNT NEEDLE CONNECTOR

[75] Inventors: Arlinda Graves, Norwalk, Conn.; Niall Sweeney, Rutherford, N.J.

[73] Assignee: Becton Dickinson and Company, Franklin Lakes, N.J.

[*] Notice: This patent is subject to a terminal disclaimer.

[21] Appl. No.: 09/249,929

[22] Filed: Feb. 12, 1999

[51] Int. Cl.[7] .................................................. A61M 25/00
[52] U.S. Cl. ......................... 604/535; 604/161; 604/162; 604/284; 604/905
[58] Field of Search .................................... 604/533–535, 604/161–162, 170, 263, 192, 284, 905

[56] References Cited

U.S. PATENT DOCUMENTS

| | | | |
|---|---|---|---|
| 4,723,948 | 2/1988 | Clark et al. | 604/283 |
| 4,747,836 | 5/1988 | Luther | 604/198 |
| 4,790,829 | 12/1988 | Bowden et al. | 604/244 |
| 4,964,855 | 10/1990 | Todd et al. . | |
| 5,192,273 | 3/1993 | Bierman | 604/174 |
| 5,281,206 | 1/1994 | Lopez . | |
| 5,376,073 | 12/1994 | Graves et al. | 604/86 |
| 5,437,648 | 8/1995 | Graves et al. | 604/263 |
| 5,496,274 | 3/1996 | Graves et al. . | |
| 5,688,254 | 11/1997 | Lopez et al. | 604/283 |
| 5,891,103 | 4/1999 | Burns | 604/192 |
| 5,910,132 | 6/1999 | Schultz | 604/162 |

OTHER PUBLICATIONS

Article entitled "The Living Hinge" Plastics Design Forum, May/Jun. 1989, p. 96.
Article entitled "Living Hinges" Injection Molding, Jun. 1998, pp. 38, 40.
"Living Hinges" Designing Plastics Parts for Assembly, 2nd Revised Edition, by Paul A. Tres, pp. 140, 141.

*Primary Examiner*—Ronald Stright
*Assistant Examiner*—Jeremy Thissell
*Attorney, Agent, or Firm*—Keith J. McWha

[57] ABSTRACT

A blunt needle connector described herein is used for transferring fluids or medication through compatible injection ports associated with primary, secondary and central lines during intravenous therapy applications. The needle connector provides needle stick protection without recessing the needle in the shield. This feature allows the end-user to better align the injection port to the needle connector and lock the needle to the injection port to eliminate line disconnects. The blunt needle connector also provides for an audible or tactile indication that the latch is secured to the intravenous fitting. This feature makes it easy to distinguish between the open or unlocked and closed or locked position of the latch. In addition, the blunt needle connector provides attachment to an intravenous line without the twisting of the line that is associated with a threaded connector.

8 Claims, 8 Drawing Sheets

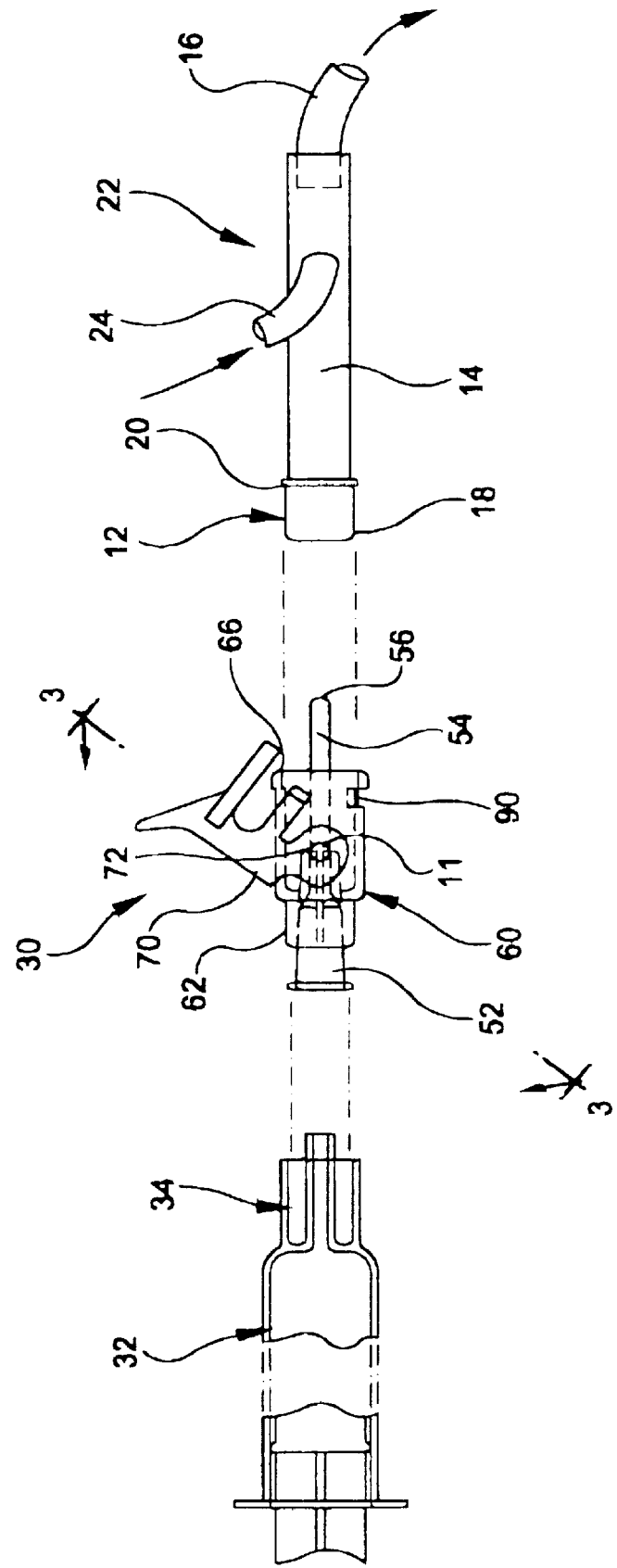

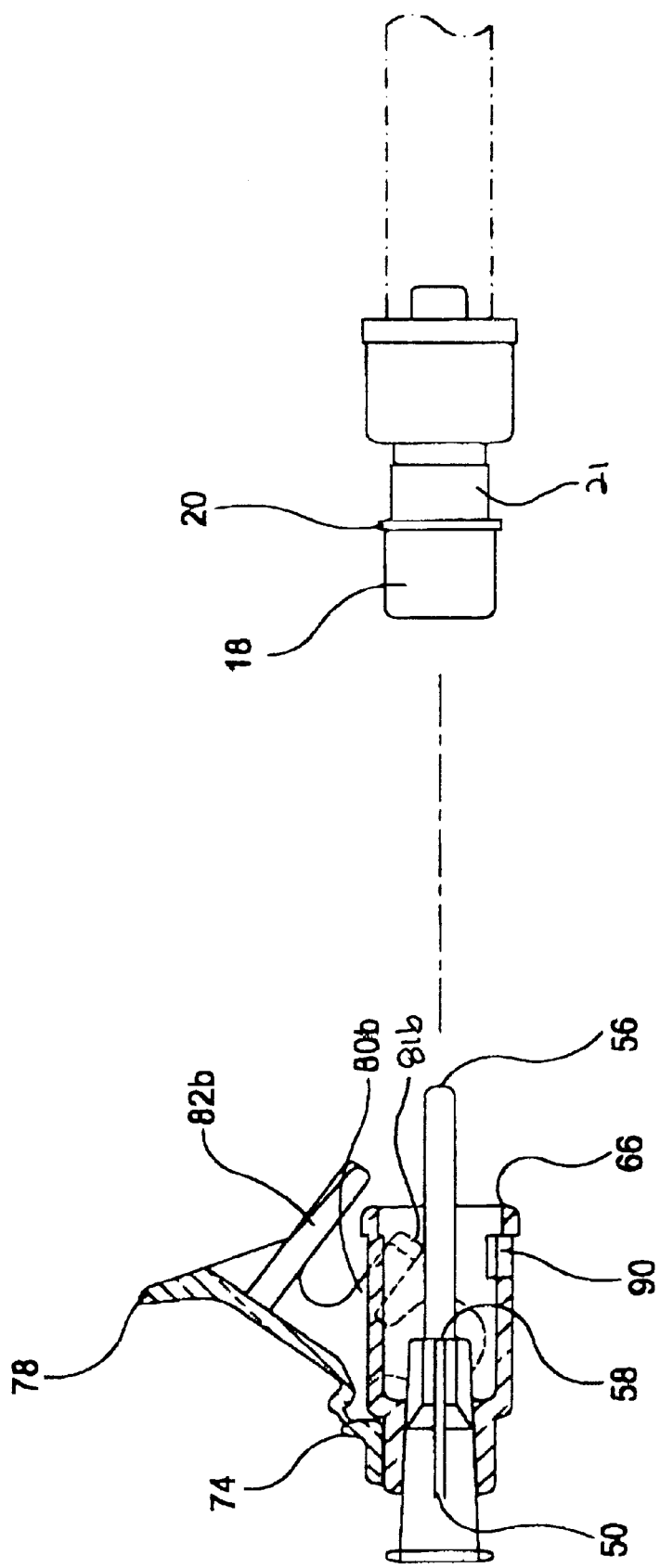

BLUNT NEEDLE CONNECTOR

BACKGROUND OF THE INVENTION

1. Field of the Invention.

This invention relates to a medical device used to connect to another medical device. More particularly, the subject invention relates to a blunt needle connector that can be safely, easily, and securely locked in communication with a fitting of an intravenous administration set.

2. Description of the Prior Art.

Intravenous sets are widely use in the prior art to provide intravenous fluid communication with a patient. The prior art intravenous sets include a needle cannula for insertion into a vein of the patient. The needle cannula communicates with one end of a flexible plastic tube, while the opposite end of the tube is connectable to a flexible bag or bottle containing the fluid to be administered to the patient.

A prior art intravenous set may also include a fitting to which a hypodermic syringe may be used for administering parenteral drugs to a patient. One example of such a fitting is known as a "straight-site". A straight-site is a relatively straight fitting, typically made from a plastic material, and includes an injection inlet carrying medication from a source in an outlet portion affixed to a tube which delivers the parenteral drug to the patient. The injection inlet usually includes a diaphragm portion, typically made of rubber or a similar compound, which can be pierced by the needle cannula of the syringe carrying the parenteral drug. The diaphragm portion, normally configured to be fitted in a fluid-tight manner to the injection inlet, typically defines a lip portion which protrudes from the stresses of the injection inlet along the outer circumference of the injection inlet.

Another example of such an intravenous fitting is known in the art as a "Y-site". A Y-site is typically a Y-shaped plastic fitting having an inlet leg, an outlet leg, and an injection leg. Like the straight-site fitting, the injection leg of the Y-site is also covered by a diaphragm defining a lip portion. The diaphragm can be pierced by the needle cannula of a syringe carrying the parenteral drug. The injection leg and the outlet leg of the prior art Y-site typically are co-linear with one another. The inlet leg typically is aligned at approximately 30 degrees to 45 degrees to the injection leg.

In use, a needle cannula of a hypodermic syringe carrying the parenteral drug to be administered is pierced through the membrane or septum of the injection inlet of the straight-site or injection leg of the Y-site. A hypodermic syringe is used in the standard manner to inject a selected dose of the parenteral drug into the injection leg. The drug is then transported to the patient by the fluid flowing from the injection inlet or leg and through the outlet portion or leg and toward the patient. A hypodermic needle is often used for introducing medication through the septum. For purposes of illustration but not of limitation, the medication delivery is implemented through the septum using a syringe. However, it will be understood that the delivery is not so limited and that many fluid delivery devices can be used to provide fluid to the needle which pierces or passes through the septum.

The potential for accidental needle sticks is further reduced by prior art needle cannula having a rigid generally cylindrical shield mounted concentrically around the needle cannula. The shield defines a diameter large enough to telescope over an injection inlet or leg of the intravenous set as the needle cannula enters the fitting. Some such shields are provided with at least one axial extended opening for receiving the inlet leg of a Y-site as the remaining portions of the shield are telescoped over the injection leg.

Although prior art protective shields as described above, can reduce the probability of accidental needle sticks, the open end of the axially extended openings still offer a potential for contact with the needle cannula. The nurse or other medical personnel utilizing the shield must manually manipulate the device to secure the shield to the injection inlet. Connecting the shield to the inlet is oftentimes done with tape. Additionally, a source of intravenous fluid intended for connection to the intravenous fitting can be accidentally disengaged either before its initial use or between successive uses. Thus, there can be a potential for both contamination of the needle cannula and/or loss of medication which can potentially be fatal to the patient.

Prior art blunt needle connectors designed to prevent accidental needle sticks oftentimes require the needle to be recesed within some protective shield. This recess of the needle cannula presents a problem of aligning the connector to the intravenous fitting. Connectors that provide threads in order to align the connector with the intravenous fitting require twisting. This twisting often results in the twisting of the intravenous line which is not preferred by the nurse or other medical personnel. Additionally, prior art blunt needle connectors are sometimes difficult to distinguish between when the connector is in the open (unlocked) position and the closed (locked) position. There is a need for some indicator to notify the user that the latch was secured to the intravenous fitting or port.

SUMMARY OF THE INVENTION

The subject of the invention is directed to a blunt needle connector for transferring fluids through an injection port during intravenous therapy applications. The blunt needle connector of the subject invention is designed so that the needle does not have to be recessed within a protective shield to prevent accidental needle sticks. Not having the needle cannula recessed allows the benefit of aligning the connector to the intravenous fitting. The blunt needle connector of the subject invention provides this alignment without the use of threads which would require twisting the intravenous fitting and the intravenous line which is not preferred. The blunt needle connector of the subject invention also allows the end user to distinguish between when the connector is in the open (unlocked) position and the closed (locked) position.

The blunt needle connector includes a blunt cannula, a shield, and a locking latch. The blunt cannula has proximal and distal ends and a lumen therethrough. The shield has a base portion where the proximal end of the blunt cannula is fixedly attached. The shield is disposed around the blunt cannula such that the distal end of the blunt cannula is partially enveloped. Thus, the needle cannula is not recessed within the protective shield. The locking latch secures the injection port partially within the shield. The locking latch has an open and closed position and is pivotably attached about the shield. When the locking latch is in the closed (locked) position, the distal end of the blunt cannula is partially enveloped. When the locking latch is in the opened (unlocked) position, the distal end of the blunt cannula is fully exposed.

The locking latch is pivotally connected to the shield either through pegs or a living hinge. In addition, the locking latch is pivotable about an axis parallel to a plane aligned with a plane defined by the base portion of the shield. The locking latch can also be pivotable about an axis substantially orthogonal to a plane aligned with a plane defined by the base portion of the shield.

The blunt needle connector is made of a thermoplastic material. An audible or tactile indication is produced when the locking latch is engaged with the shield. In addition, the locking latch is configured to maintain a stable open position against the shield and retains the locking latch in a stable closed position when engaged with the shield. The intravenous fitting can be a straight site or a Y-site. Both the straight site and the Y-site have an injection port.

BRIEF DESCRIPTION OF THE DRAWINGS

FIG. 2 is an exploded elevational view of the blunt needle connector in accordance with the subject invention in combination with a hypodermic syringe and a Y-site fitting for an intravenous set;

FIG. 9 illustrates the blunt needle connector with the latch affixed to the shield via a living hinge arrangement.

DETAILED DESCRIPTION

Figure 1:
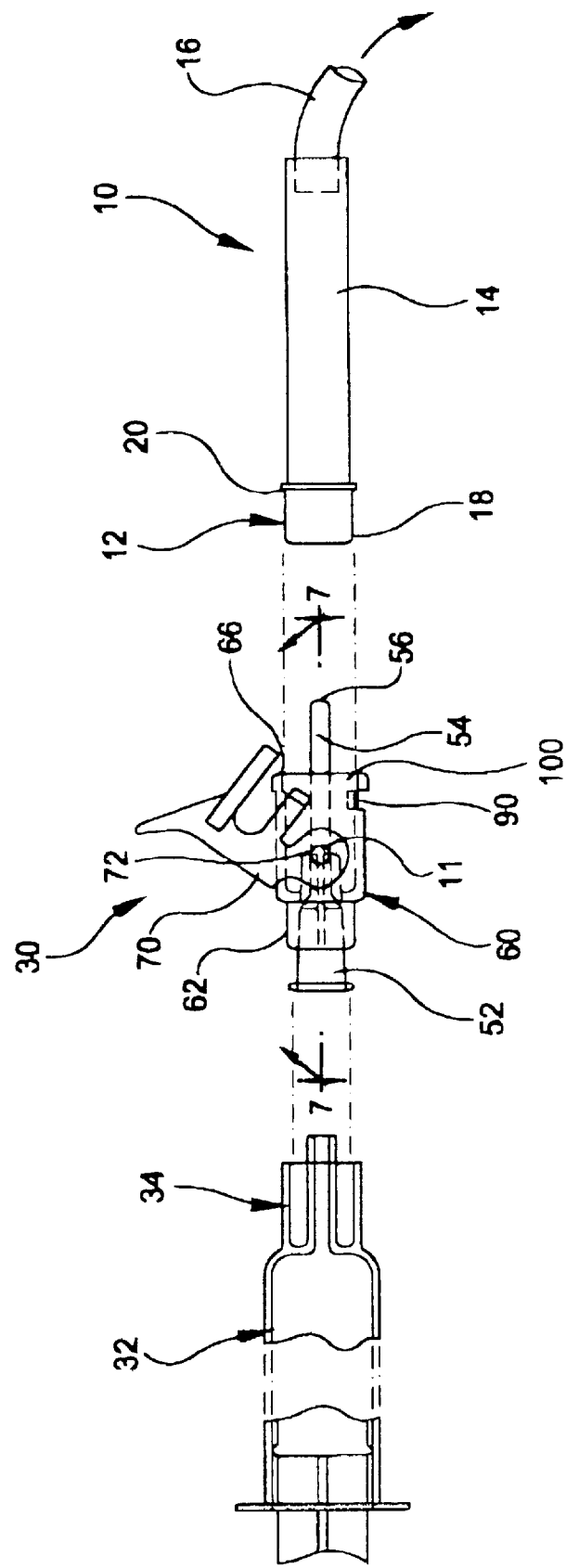
FIG. 1 is an exploded elevational view of the blunt needle connector in accordance with the subject invention in combination with a hypodermic syringe and a straight-site fitting for an intravenous set.

While this invention is satisfied by embodiments in many different forms, there are shown in the drawings and will be herein described in detail preferred embodiments of the invention with the understanding that the present disclosure is to be considered exemplary of the principles of the invention. This disclosure is not intended to limit the scope of the invention to the embodiments illustrated. The scope of the invention is outlined by the attached claims and their equivalents.

Adverting to the drawings, a blunt needle connector 30 is used for transferring fluids through compatible injection ports associated with primary, secondary, and central lines during intravenous therapy applications. The blunt needle connector is preferably used with a medical delivery device, such as a hypodermic syringe 32, for delivery of a parenteral drug through an intravenous fitting. The intravenous fitting may be a straight site fitting 10 (FIG. 1) or a Y-site fitting 22 (FIG. 2). For ease of reference and explanation, operation of the device will be explained principally in reference to the straight site fitting. However, it will be understood by those skilled in the art that the invention is not so limited and that the blunt needle connector is readily applicable to the Y-site fitting.

Referring to FIGS. 1 and 2, the hypodermic syringe or another fluid delivery device such as a piggyback intravenous set, can be used with the blunt needle connector. The syringe has a distal end 34 which can securely slip fit onto the blunt needle connector or removably lock onto the blunt needle connector.

The straight site fitting in FIG. 1 includes an injection port 12 and an outlet port 14 affixed to tube 16 for delivery of fluid to a patient. The fluid can be a parental medication or any other fluid used in intravenous therapy applications. The Y-site in FIG. 2 has an inlet leg 24 which extends to the Y-site from a supply of fluid to be delivered intravenously to the patient.

In either of the fittings described in FIGS. 1 and 2, the injection port is intended for use as a port for delivering fluid or medication to the patient. A diaphragm portion 18, such as a pre-slit septum or pierceable septum, is provided for sealing the injection port of the straight site fitting or the Y-site fitting. The diaphragm portion is penetrable by a needle cannula to enable selective communication of a parenteral medication through the injection port and into the stream of fluid being delivered intravenously to the patient.

The blunt needle connector of the subject invention may include a needle hub 52 having a blunt cannula 54 securely attached. The blunt cannula includes a distal end 56, a proximal end 58 and a lumen 50 therethrough. The needle hub is threadly engageable with the distal end of the syringe or can be securely slip fitted. The connection enables fluid communication from the syringe to the lumen of the blunt cannula.

Averting to FIGS. 1–9, the blunt needle connector further includes a shield 60 having a base portion 62 partially but securely and permanently mounted over the distal end of the blunt cannula. Preferably, the blunt cannula is not fully recessed within the shield. This configuration allows alignment of the blunt cannula or blunt needle connector with the injection port of the intravenous fitting.

The blunt cannula drastically reduces the risk of inadvertent needle stick injury by its blunt configuration. Having the shield not extend beyond the distal end of blunt cannula allows alignment of the blunt needle connector and the intravenous fitting. Threaded connectors allow alignment between the connector and fitting. However, threaded connectors twist the intravenous line which is not preferred. The present invention allows alignment without the intravenous line being twisted. In addition, the blunt cannula drastically reduces the risk of inadvertent needle stick injury as compared to conventional cannula since its configuration is blunt and not sharp.

The shield's primary purpose is to provide structure for a locking latch 70 to be hingedly mounted and removably but securely attached to the shield. As will be described, a portion of the latch securely connects the intravenous fitting to the blunt needle connector. The shield features a depression 90 which allows the locking latch to be removably secured to the shield during connection of the fitting and blunt needle connector. By having the latch being removably secure allows the end-user to change intravenous lines during the intravenous application therapy. However, it is within the scope of this invention to have the latch permanently attach to the shield when securing the intravenous fitting to the blunt needle connector. Such configuration may be desired for short-term intravenous therapy where the intravenous line is not being changed.

Figure 6:
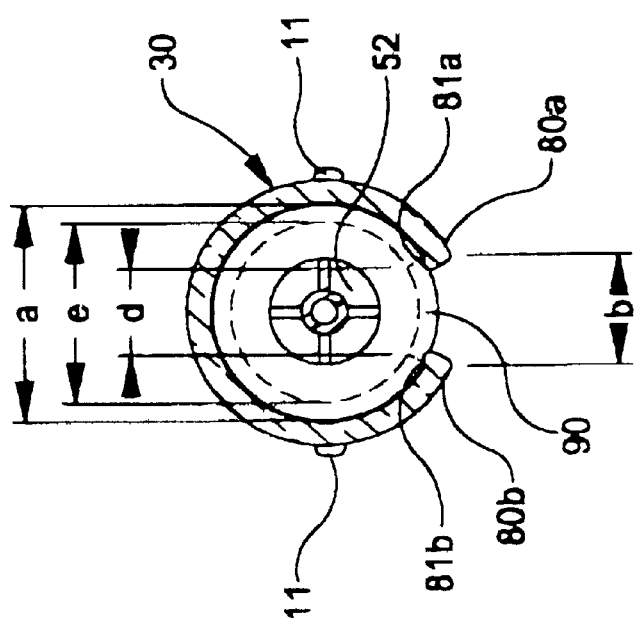
FIG. 6 is a back elevational view of the latch as viewed from the left side of FIG. 1.
Figure 5:
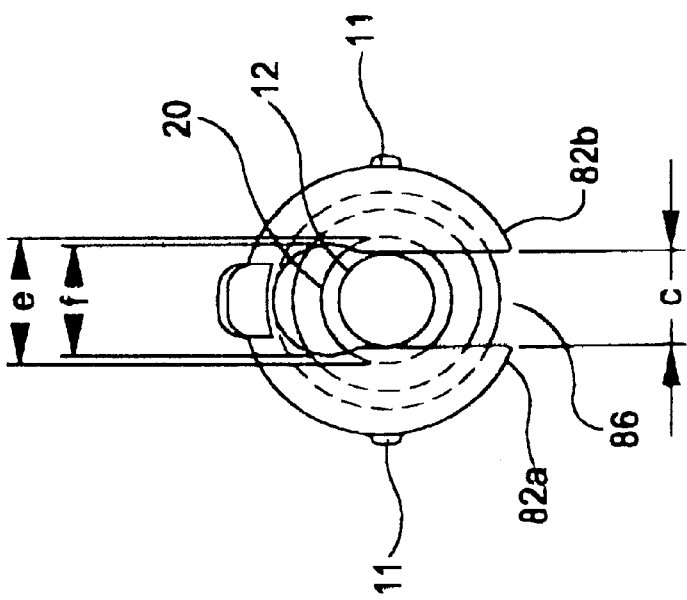
FIG. 5 is a front elevational view of the latch as viewed from the right side of FIG. 1.
Figure 7:
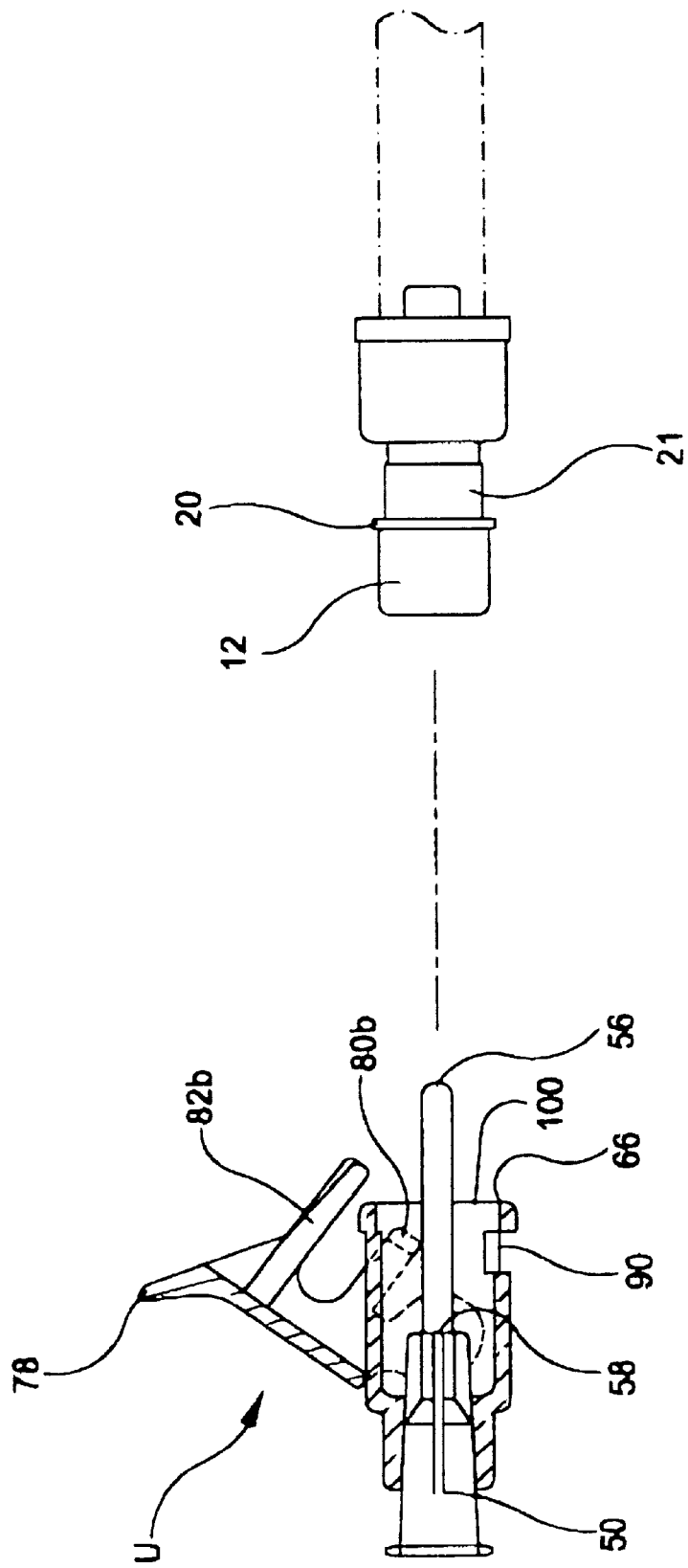
FIG. 7 is a cross-sectional view taken along line 7—7 in FIG. 1 depicting the blunt needle connector prior to engagement with the fitting.

The shield also features a distal end 66 and a clearance portion 100. As shown in FIGS. 5, 6, and 7 the clearance portion has a larger diameter "a" than diameter "e" of the injection port of the intravenous fitting. This configuration allows the injection port but not lip portion 20 of the injection port to enter the blunt needle connector through the distal end of the shield with substantial clearance thereby allowing alignment of both the intravenous fitting with the blunt needle connector and the blunt cannula. This configuration is shown in FIG. 7.

Additionally, the distal end of the shield is preferably configured so that when the intravenous fitting is secured to the blunt needle connector the injection port is only partially within the shield. This configuration gives the end-user visibility to obtain alignment of the blunt needle connector or blunt cannula with the injection port of the intravenous fitting. Also this feature provides for more control of attaching and securing the intravenous fitting to the blunt needle connector or blunt cannula without being encumbered by the distal end of the shield.

As shown in FIGS. 1–9, the blunt needle connector also includes a locking latch 70 hingedly connected to shield 60 at a pivot location 72. The latch is hingedly mounted for rotation about an axis orthogonal to the blunt needle cannula and lying in or parallel to a plane passing centrally through the longitudinal midpoints of the shield. The shield has at least one peg or protrusion as shown in FIGS. 1, 5, and 6 that hingedly connects to the shield at the pivot location.

As will be realized by those skilled in the art, in lieu of pivot connection 72, a plastic living hinge 74 (FIG. 9) may connect the locking latch and the shield for allowing pivoted rotation of the latch with respect to the shield. Living hinges as shown in FIG. 10 can be described as a bridge with length "l" and thickness "t" and a recess "R" in the upper portion with an arc "A" in the upper portion.

Figures 10, 11:
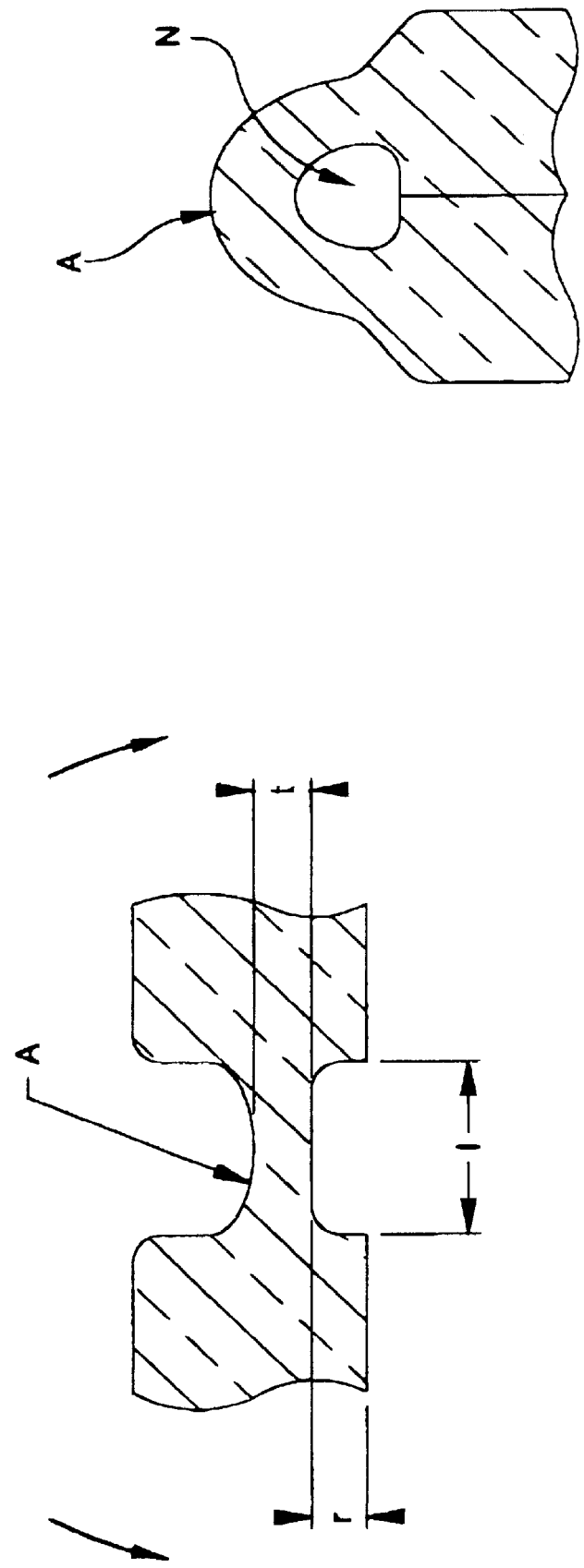
FIG. 10 is an enlarged view of the living hinge arrangement in FIG. 9.
FIG. 11 is an enlarged view of the living hinge arrangement in FIG. 9 when the latch is in the closed or locked position.

When the hinge is closed as shown in FIG. 11, the recess forms a notch "N" that creates the necessary radius to prevent a possible crack that could break the hinge. The arc is designed to provide the orientation of the thermoplastic molecules and enable the hinge to withstand many flexure cycles. A typical hinge length is about 0.060 inches (15 mm) with the thickness of about 0.008 to about 0.015 inches (0.2 to 0.4 mm). These proportions usually give an acceptable balance of flexibility and stiffness. All corners of the hinge area have radii to reduce stress concentrations. Typical radii are about 0.030 inches (0.75 mm). The recessed depth "r" is typically about 0.005 to about 0.010 inches (0.13 to 0.25 mm). The recess allows the mating parts to fit properly and prevent a sharp fold on the hinge when closed.

The first time the hinge is flexed, the hinge length will neck down and undergo plastic yielding. If this is done a few times immediately after manufacturing while the part is still warm, the material in the hinge will orient in the proper direction and increase the fatigue life. A parameter in ensuring long fatigue life without failure is the ratio of the hinge thickness to hinge length. A ratio between about 0.13 and about 0.25 is recommended. It will be appreciated by those skilled in the art that living hinges can be molded in the part, stamped, and incorporated in the part by various techniques. The subject invention is not limited to the specific embodiment shown and given merely as an example.

Figure 8:
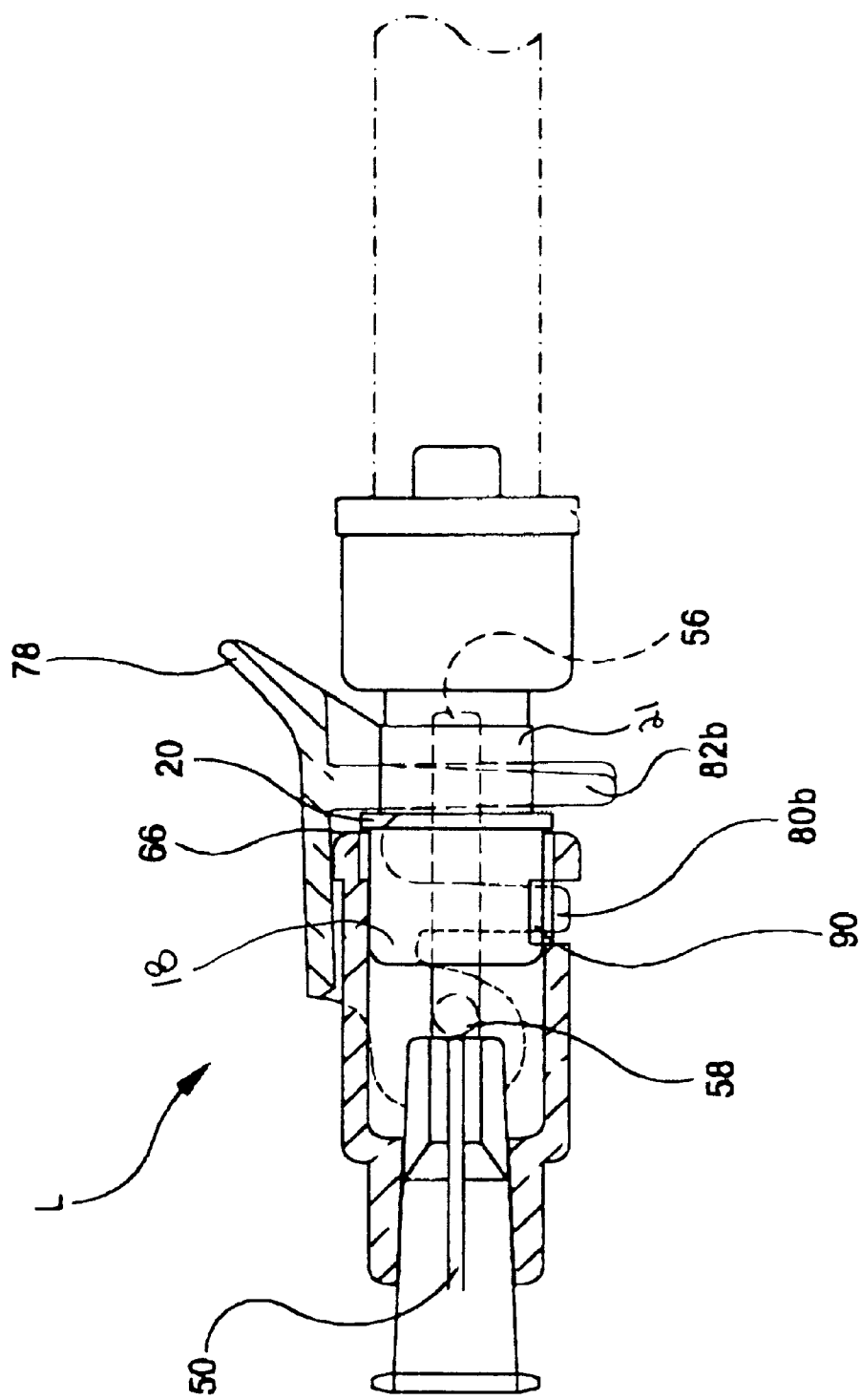
FIG. 8 illustrates the blunt needle connector of FIG. 7 shown after engagement with the fitting and depicting retention of the fitting partially within the shield.

FIGS. 3–6 show locking latch 70 which includes a pivot arm 76 which extends generally distally from pivot point 72 and terminates in an actuating projection 78. The actuating projection is dimensioned and configured to enable the pivoting movement to be generated easily by a thumb or a forefinger. The latch further features means for securing the latch with the shield and means for securing the fitting partially within the shield. For purposes of illustration only, two finger members 80a, b and two flanges 82a, b project outward from the pivot arm in a circumferential manner. The finger members secure the latch to the shield in the closed or locked position "L" as shown in FIG. 8.

The flanges secure the intravenous fitting partially within the shield. Each of the finger members and flanges can be manufactured integrally with the latch. It will however be understood by those skilled in the art that both may be configured in various manners. For example, a single finger member and a single flange may be provided in lieu of the respective pairs to serve the same purpose. Other variants within the ambit of the skilled artisan are possible.

Figure 4:
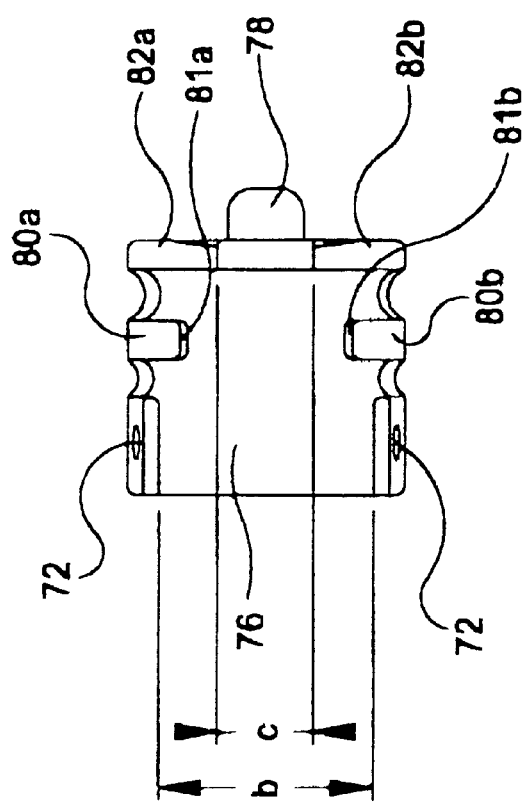
FIG. 4 is a bottom elevational view of the latch.
Figure 3:
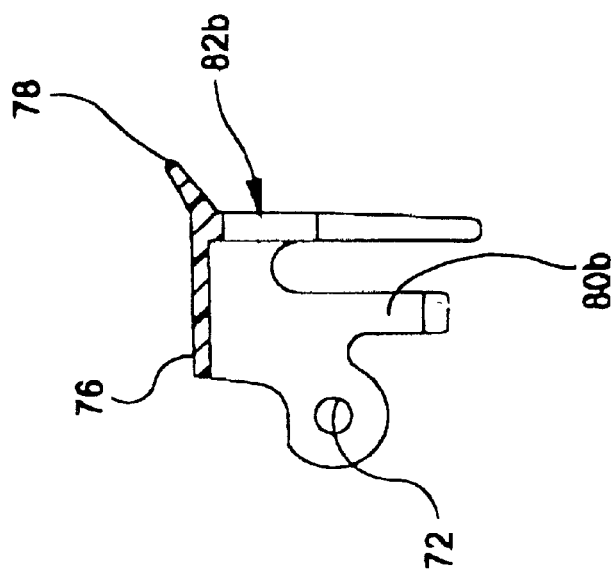
FIG. 3 is a side cross-sectional plan view taken along lines 3—3 in FIG. 2 of the latch of the blunt needle connector.

The locking latch is preferably formed of a thermoplastic material so that the fingers and the flanges are resiliently expandable and contractible at their juncture with the pivot arm in a manner to hinge about pivot arm. Finger members 80a, b further include respective ramping portions 81a, b as shown in FIG. 4. The ramping portions snap into depression 90 of the shield in the closed or locked position to secure the locking latch to the shield and the flanges around the intravenous fitting. The depression has a width "d" which is wide enough to accept the ramping portions. It is well understood by one skilled in the art that the ramping portions can be configured for a permanent lock or removable lock in the depression of the shield based on the geometry of the ramping portions and the depression in the shield.

The finger members are separated by a width "b" such that the outside diameter of injection port 12 does not substantially have any interference with the finger members. Also, the width is dimensioned so that the finger members in the closed or locked position do not allow lip portion 28 to pass further toward the proximal end of the blunt cannula. Flanges 82a, b are separated by slot 86 which has a width "c" as shown in FIG. 5.

The flanges are dimensioned so that in the closed or locked position the flanges substantially interfere with lip portion 28. In addition, the shield is configured such that the clearance portion has a larger diameter "a" than diameter "e" of the injection port of the intravenous fitting. But, diameter "a" has a smaller diameter than diameter "f" of the lip portion of the injection port. This configuration allows the injection port but not lip portion 20 of the injection port to enter the blunt needle connector through the distal end of the shield. It also provides for the locking latch to secure the injection port partially within the shield. Thus, in the closed or locked position, the lip portion of the injection port is locked between the finger members and the flanges.

Also, in the closed or locked position, the flanges partially envelop the blunt cannula such that the blunt cannula protrudes distally beyond the closed flanges. This geometry provides for stability of the intravenous fitting when connected to the blunt needle connector and it furthers the purpose of alignment between the blunt cannula or blunt needle connector and the intravenous fitting.

Operation of the blunt needle connector is relatively straightforward and will now be generally explained referring to FIGS. 7 and 8. The blunt needle connector can be used by initially connecting the needle hub to the distal end of the syringe. The blunt needle connector can then be employed with the intravenous fitting, like the straight site fitting, by inserting the injection port partially into the shield until it stops due to the interference between the shield and the lip portion as previously explained. The distal end of the blunt cannula then pierces through the diaphragm portion of the injection port. As seen in FIG. 7 and 8, when the blunt needle connector goes from the open or unlocked "U"

position to the closed or locked position "L" the injection port and diaphragm portion is partially seated in the shield. This feature allows visibility and manual maneuvering to align the blunt cannula to the injection port.

After aligning and seating the injection port on the blunt cannula, the locking latch is rotated about the pivot point and toward the shield. Rotation of the pivot arm toward the shield urges ramping portions of the finger members into sliding engagement with the depression of the shield. Thus, removably retaining the locking latch to the shield. The deflection and subsequent engagement of the ramping member can be configured to provide a distinct audible or tactile indication that the locking latch is in the closed position. Similarly, the deflection and subsequent resilient return of the locking latch in response to the opening forces exerted on the latch may also generate a distinct audible and tactile indication that the locking latch is in the open position.

Simultaneously, as the locking latch is rotated, the flanges are urged to retain the injection port partially within the shield. Rotation of the flanges causes the flanges to approach distal end 21 of the injection port. The surface of the distal end forces deflection of the flanges around the injection port. This deflection causes width "c" to expand. Further rotation of the locking latch allows the flanges to constrict and secure the injection port. This constriction causes width "c" to return to its original dimension. At this point the lip portion is captured by the flanges securing the intravenous site to the blunt needle connector. Because width "c" is less than the width of the lip portion, the lip will be prevented from inadvertent withdrawal from the blunt needle connector.

As previously noted, the blunt needle connector is equally amenable to use with either a straight-site fitting or a Y-site fitting. However, in both configurations, the blunt cannula, injection port 12, diaphragm portion 18 and lip portion 20 are not recessed within the shield. This feature provides for alignment with the intravenous site and manual maneuverability and visibility to accomplish this alignment. Additionally, both configurations provide for when the blunt needle connector is in the closed or locked position "L" there is partial enclosure of injection port 12, diaphragm portion 18 and lip portion 20 within the shield and secure engagement of the blunt needle connector with the intravenous fitting. This feature provides for visibility and confirmation of the alignment between the blunt cannula or blunt needle connector and the intravenous fitting.

Also, both configurations in the closed or locked position, the flanges partially envelop the blunt cannula such that the blunt cannula protrudes distally beyond the closed flanges. This geometry provides for stability of the intravenous fitting when connected to the blunt needle connector and it furthers the purpose of alignment between the blunt cannula and the intravenous fitting. Because the cannula is blunt the risk of inadvertent needle sticks is drastically reduced. Both configurations in the closed or locked position also provide for distal end 21 of the injection port to protrude distally beyond the closed flanges. This feature provides additional visual assurance of the alignment between the connector and the fitting.

What is claimed is:

1. A blunt needle connector, comprising:

an intravenous fitting having an injection port, said injection port having a lip portion;

a blunt cannula having proximal and distal ends and a lumen therethrough;

a shield defining a base portion and having a distal end and a clearance portion, said shield disposed around said blunt cannula such that said blunt cannula is partially enveloped, said proximal end of said blunt cannula fixedly attached to said base portion, said clearance portion sized greater than said injection port and sized smaller than said lip portion such that said injection port enters said distal end of said shield and said lip portion cannot enter said distal end; and a locking latch for securing said injection port partially within said shield, said locking latch having an open and closed position and being pivotally attached about said shield, such that when said locking latch is in said closed position, said distal end of said blunt cannula is partially enveloped by said latch and when said locking latch is in said open position said distal end of said blunt cannula is fully exposed.

2. The blunt needle connector as recited in claim 1, wherein the locking latch is pivotably connected to said shield via a living hinge.

3. The blunt needle connector as recited in claim 1, wherein said intravenous fitting is a straight site.

4. The blunt needle connector as recited in claim 1, wherein said intravenous fitting is a Y-site.

5. The connector as recited in claim 1, wherein said locking latch is pivotable about an axis substantially orthogonal to a plane aligned with a plane defined by said base of said shield.

6. The connector as recited in claim 1, wherein said blunt cannula is made of a thermoplastic material.

7. The connector as recited in claim 1, wherein an audible or tactile indication is produced when said locking latch is engaged with said shield.

8. The connector as recited in claim 1, wherein said locking latch is configured to maintain in a stable open position against said shield and to retain said locking latch in a stable closed position when engaged with said shield.

* * * * *